US012629134B2

(12) United States Patent
Sheeran et al.

(10) Patent No.: US 12,629,134 B2
(45) Date of Patent: May 19, 2026

(54) USER INTERFACE AND METHOD OF SETTING ACQUISITION PRIORITY IN INTERLEAVED IMAGING MODES OF ULTRASOUND IMAGING

(71) Applicant: KONINKLIJKE PHILIPS N.V., Eindhoven (NL)

(72) Inventors: Paul Sheeran, Woodinville, WA (US); Thanasis Loupas, Kirkland, WA (US); Charles Tremblay-Darveau, Seattle, WA (US); Chris Loflin, Lynnwood, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 49 days.

(21) Appl. No.: 18/288,261

(22) PCT Filed: Apr. 25, 2022

(86) PCT No.: PCT/EP2022/060810
§ 371 (c)(1),
(2) Date: Oct. 25, 2023

(87) PCT Pub. No.: WO2022/229047
PCT Pub. Date: Nov. 3, 2022

(65) Prior Publication Data
US 2024/0206850 A1     Jun. 27, 2024

Related U.S. Application Data

(60) Provisional application No. 63/180,887, filed on Apr. 28, 2021.

(51) Int. Cl.
*A61B 8/00* (2006.01)
*G01S 7/52* (2006.01)
*G01S 15/89* (2006.01)

(52) U.S. Cl.
CPC .............. *A61B 8/48* (2013.01); *A61B 8/4488* (2013.01); *A61B 8/465* (2013.01); *A61B 8/467* (2013.01);
(Continued)

(58) Field of Classification Search
CPC ......... A61B 8/48; A61B 8/4488; A61B 8/465; A61B 8/467; G01S 7/52085; G01S 7/52098; G01S 15/8915; G01S 15/8979
See application file for complete search history.

(56) References Cited

U.S. PATENT DOCUMENTS 6,045,505 A     4/2000  Holley et al.
6,443,896 B1    9/2002  Detmer
(Continued)

FOREIGN PATENT DOCUMENTS

JP     2008272033 A    11/2008
JP     2010029727 A     2/2010
(Continued)

OTHER PUBLICATIONS

International Search Report and Written Opinion for PCT/EP2022/060810; Mailing date: Jul. 27, 2022, 11 pages.

*Primary Examiner* — Dixomara Vargas

(57)     ABSTRACT

Ultrasound imaging system and method that provides user- or situationally-adjustable interleaved imaging modes are described. An ultrasound system according to the present disclosure includes a user interface that enables the user to interact with the system to specify or otherwise control the priority of one mode of the other modes in a multi-mode imaging operation.

16 Claims, 11 Drawing Sheets

(52) U.S. Cl.
    CPC ...... *G01S 7/52085* (2013.01); *G01S 7/52098*
        (2013.01); *G01S 15/8915* (2013.01); *G01S*
             *15/8979* (2013.01)

(56) References Cited

U.S. PATENT DOCUMENTS

| | | | |
|---|---|---|---|
| 6,530,885 | B1 | 3/2003 | Entrekin et al. |
| 2007/0161904 | A1 | 7/2007 | Urbano |
| 2012/0059262 | A1* | 3/2012 | Clark .................. G01S 7/52084 |
| | | | 600/440 |
| 2013/0345564 | A1* | 12/2013 | Nakaya ............... A61B 8/5246 |
| | | | 600/440 |
| 2015/0087980 | A1 | 3/2015 | Yao et al. |
| 2017/0231599 | A1* | 8/2017 | Jago ..................... A61B 8/5207 |
| | | | 600/438 |
| 2019/0142380 | A1* | 5/2019 | Emery ................. A61B 8/4483 |
| 2019/0239857 | A1 | 8/2019 | Nakajima |
| 2020/0158843 | A1* | 5/2020 | Schmied ............... A61B 8/483 |

FOREIGN PATENT DOCUMENTS

| | | | |
|---|---|---|---|
| WO | 2006002625 | A1 | 1/2006 |
| WO | 2018178220 | A1 | 10/2018 |

* cited by examiner

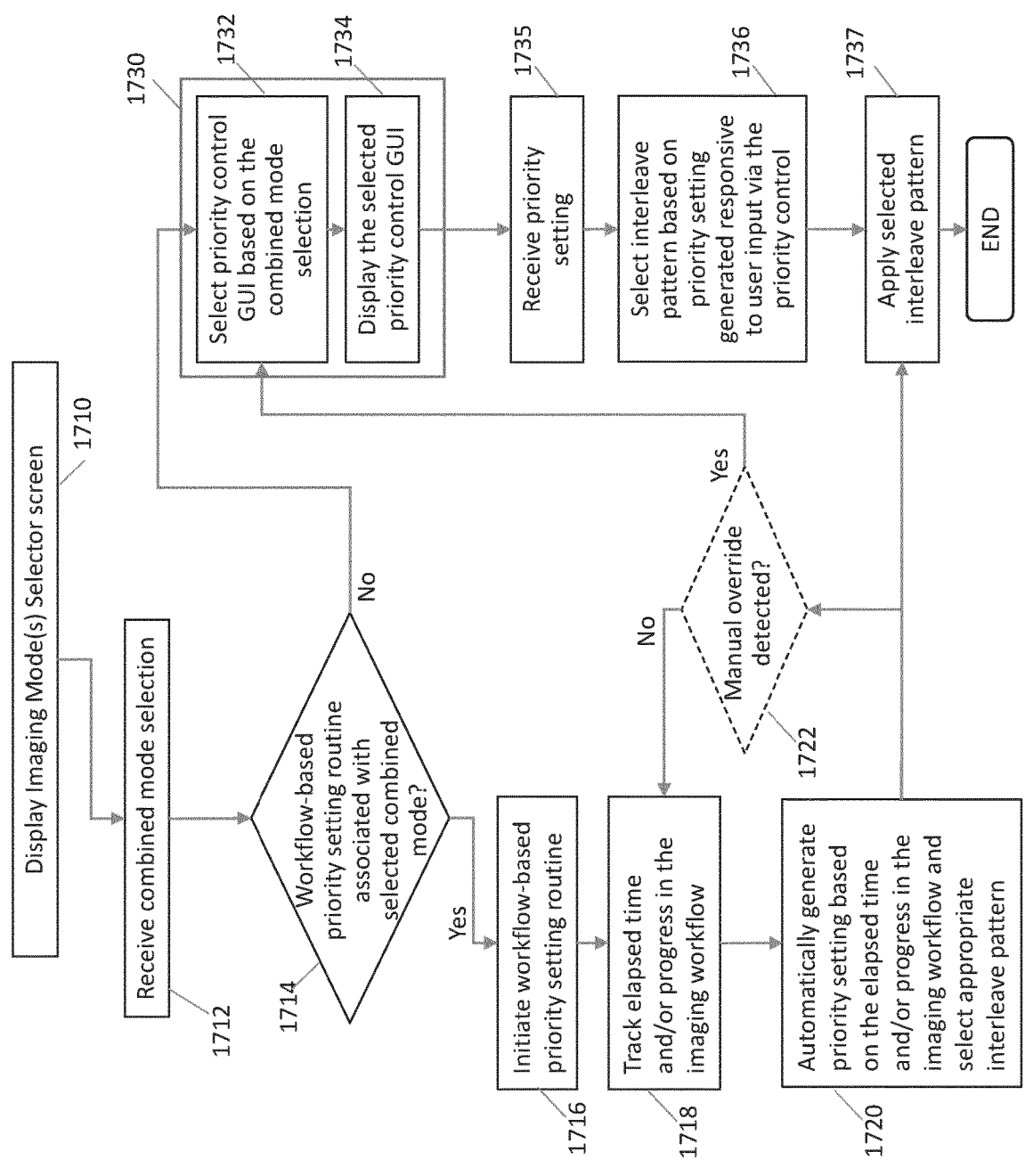

1700

Display Imaging Mode(s) Selector screen — 1710

Receive combined mode selection — 1712

Workflow-based priority setting routine associated with selected combined mode? — 1714

No →

1730

Select priority control GUI based on the combined mode selection — 1732

Display the selected priority control GUI — 1734

Receive priority setting — 1735

Select interleave pattern based on priority setting generated responsive to user input via the priority control — 1736

Apply selected interleave pattern — 1737

END

Yes →

Initiate workflow-based priority setting routine — 1716

Track elapsed time and/or progress in the imaging workflow — 1718

Automatically generate priority setting based on the elapsed time and/or progress in the imaging workflow and select appropriate interleave pattern — 1720

Manual override detected? — 1722

No →

Yes →

FIG. 17

USER INTERFACE AND METHOD OF SETTING ACQUISITION PRIORITY IN INTERLEAVED IMAGING MODES OF ULTRASOUND IMAGING

CROSS-REFERENCE TO PRIOR APPLICATIONS

This application is the U.S. National Phase application under 35 U.S.C. § 371 of International Application No. PCT/EP2022/060810, filed on Apr. 25, 2022, which claims the benefit of U.S. Provisional Patent Application No. 63/180,887, filed on Apr. 28, 2021. These applications are hereby incorporated by reference herein.

FIELD OF THE INVENTION

The present disclosure relates generally to ultrasound imaging and, in particular, to a method and system that provides a user interface for setting acquisition priority in multi-mode ultrasound imaging.

BACKGROUND OF THE INVENTION

Ultrasound imaging systems have been developed, which interleave the acquisitions of different imaging modes for multi-mode imaging. However, in existing systems this interleaving can present challenges relating to frame-rate. In existing systems, the manner in which the acquisitions are interleaved is often based on a default configuration that is preprogrammed into the system and cannot be altered by the user. When several imaging modes are combined, such as contrast+Doppler+tissue sequences made recently available in certain systems, overall frame rates can be quite low. The frame-rate limitations are especially exacerbated in certain modes, such as real-time 3D modes, which are extremely frame-rate limited as a result of the physical time required to sample a full volume. Interleaving in complex imaging modes, such as 3D Doppler and contrast, can become difficult to use because the refresh rate is low and motion susceptibility is high. Thus, developers and manufactures of ultrasound imaging systems continue to seek improvements thereto.

SUMMARY OF THE INVENTION

While ultrasound imaging systems have been developed to provide the ability to combine multiple imaging modes, frame-rate limitations exists on these systems. Ultrasound imaging systems and methods according to embodiments of the present disclosure provide interleaved imaging modes with user- and/or situationally-adjustable acquisition priority.

An ultrasound imaging system according to some embodiments of the present disclosure includes a transmit/ receive controller, which is configured to be communicatively coupled to a transducer array to cause the transducer array to transmit and receive ultrasound for imaging concurrently in a plurality of imaging modes. When the transmit/receive controller is set, typically responsive to user input, to cause the array to acquire ultrasound signals concurrently for multiple modes, this is referred to herein as a multi-mode imaging. The ultrasound imaging system also includes a processor configured to generate, in real-time, images associated with some or all of the multiple imaging modes from the signals received from the transducer array. The ultrasound imaging system further includes a memory storing at least one of: a plurality of predetermined interleave patterns, and a set of predefined rules for determining an interleave pattern and a user interface comprising at least one user control for prioritizing one of the plurality of imaging modes over remaining ones of the plurality of imaging modes. The processor of the ultrasound imaging system is further configured, responsive to receiving a priority setting, to select one of the plurality of predetermined interleave patterns or to determine an interleave pattern that increases a frame rate of the prioritized one of the plurality of imaging modes, and the transmit/receive controller causes the transducer array to transmit and receive ultrasound in accordance with the interleave pattern selected or determined by the processor.

A method of concurrent ultrasonic imaging in a plurality of imaging modes according to some embodiments includes receiving, by a processor of an ultrasound imaging system, a combined mode selection specifying the plurality of imaging modes, receiving a priority setting that selectively sets a priority of one of the plurality of imaging modes relative to other ones of the plurality of imaging modes, selecting, from among a plurality of interleave patterns associated with the plurality of imaging modes, an interleave pattern that corresponds to the priority setting, applying the selected interleave pattern, via a transmit controller, to a transducer array to selectively activate elements of the array in accordance with a sequence defined by the selected interleave pattern for concurrently acquiring images associated with each of the plurality of imaging modes, and displaying, in real-time, the images associated with each of the plurality of imaging modes.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 17 is a flow diagram of a process for prioritizing one of a plurality of imaging modes when concurrently imaging in the plurality of imaging modes.

DETAILED DESCRIPTION OF THE EMBODIMENT

Figure 1:
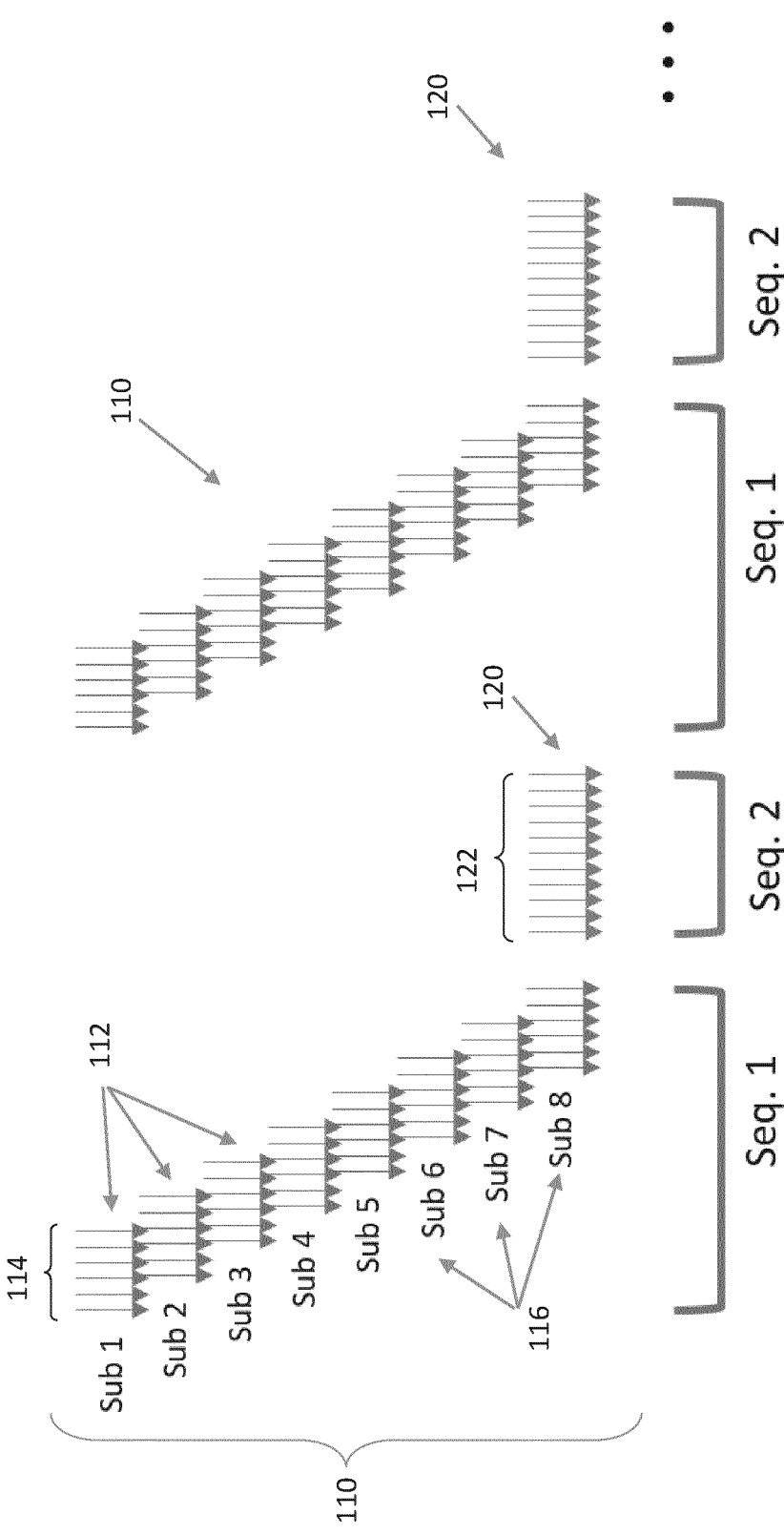
FIG. 1 shows an interleave pattern for interleaving the acquisition sequences of a 3D imaging mode and a 2D imaging mode for concurrently imaging in the two imaging modes.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that features, components, and/or steps described with respect to one embodiment may be combined with features, components, and/or steps described with respect to other embodiments of the present disclosure. The numerous such combinations may not be described separately herein for the sake of conciseness and clarity.

Examples according to the present disclosure present systems and methods for selectively optimizing the frame-rate of at least one imaging mode when imaging in a plurality of imaging modes concurrently. Ultrasound imaging systems have been introduced that can image in multiple imaging modes concurrently and when a multi-mode imaging is selected on the system, the acquisitions associated with the two or more modes are interleaved and then processed to be displayed simultaneously to the user (e.g., side by side or through overlays). Examples of these are Doppler, contrast and elastography, which are modes commonly imaged with B-mode (or tissue) imaging. In some cases, achieving high frame-rates can be challenging—especially in real-time 3D (4D) applications. In accordance with the present disclosure, systems and methods use a user-adjustable acquisition priority that changes the interleave rate between two or more sequences in order to increase frame-rate in one of the sequences at the expense of the other(s). In some embodiments, additionally or alternatively this acquisition priority may be adjusted automatically through an imaging protocol or workflow, such as in contexts where the protocol or workflow serves as a standard workflow for the particular imaging application. While primarily envisioned for applications which are more significantly frame-rate limited (e.g. volume flow, real-time 3D contrast, contrast+Doppler+tissue), the elements of the present invention may be applied to virtually any other multi-mode imaging application.

A typical 2D image frame (or simply 2D image or frame) may be formed from a large number of image (or scan) lines, each line being acquired by a pulse-echo sequence, also referred to as a transmit/receive event. For example, a typical 2D B-mode image may consist of a large number (e.g., on the order of 80) image lines produced by a corresponding number of transmit/receive events in the same azimuthal plane. These scan lines are assembled together to form the 2D image. In real-time imaging, the 2D image on the display may be refreshed in real-time, that is as new imaging data is acquired and new frames of the 2D image are generated by the imaging system, and this refreshing of the image may be referred to as frame rate (or temporal resolution). In order to construct a 3D image frame, the collection of pulse-echo sequences, in the present example, the approximately 80 transmit/receive events sequence, is repeated a sufficient number of times, for example anywhere between 30 to 70 times, each time in a slightly different elevation plane, producing in this example 30 to 70 2D image frames that collectively make up a single 3D image frame corresponding to the imaged volume. Alternatively, the transmit/receive events for each image line in the volume may be acquired in different order, as long as a sufficient number of image lines, collected across the different azimuthal and elevation locations, are acquired to produce the full 3D image frame. Like in 2D imaging, when performing real-time 3D imaging (often referred to as 4D imaging), the sequence for acquiring all of the image lines of the volumetric region is repeated and the displayed image is refreshed at a given frame rate (or temporal resolution), which may be affected, in part, by the desired spatial resolution (e.g., the number of scan lines and/or scan planes into which the volumetric region is divided). When imaging in multiple modes concurrently the acquisition (i.e., transmit/receive event) sequences of each mode are combined, in some cases by being sequentially interleaved, such that the acquisition sequence for acquiring a single frame of one mode follows the completion of the acquisition sequence for acquiring a single frame of the other mode, and in other cases by subdividing a full sequence for a frame into ensembles which are interleaved with acquisitions of another mode. As the number of transmit/receive events in a frame sequence increases, particularly when imaging in 3D and/or when more than 2 modes are combined, the temporal resolution of some of the modes may be unacceptable and/or the user may be unwilling to sacrifice frame rate of one mode in order to obtain some critical or desired frame rate. Currently no mechanisms are provided on existing systems to enable the user and/or system to selectively adjust the frame rate of one or a subset of the modes in a multi-mode imaging operation. Some of the examples herein may provide solution(s) to the shortcomings in the art in this regard.

FIG. 1 illustrates an example of a multi-mode imaging operation in which image frames for two different imaging modes are acquired together. The first acquisition sequence, Seq. 1, is associated with a 3D imaging mode (e.g., 3D contrast imaging), while the second acquisition sequence, Seq. 2, is associated with a 2D imaging mode (e.g., 2D B-mode, also referred to as tissue, imaging). The first sequence Seq. 1 is configured for acquiring a 3D data set corresponding to a 3D frame 110 (e.g., a 3D contrast image frame) of an imaged volume (e.g., a volume of biological tissue). In this example, the 3D frame 110 is composed of multiple scan planes 112, each composed of multiple scan lines 114. The collection or set of scan lines 114 associated with each scan plane 112 is produced by a corresponding sub-sequence (e.g., Sub 1 through Sub n) of the Seq. 1 that results in a full 3D image frame. For simplicity of illustration, only 6 individual scan lines 114 are shown for each sub sequence 116, however it will be understood that in most real life applications, the number of scan lines for acquiring a single 2D frame would be significantly higher, e.g., between 50-100 lines. Similarly, only 8 sub-sequences are shown for simplicity, however in it will be understood that in most real life applications, the number of scan planes forming a full 3D image frame would greater than 8, for example on the order of 30-70 scan planes. Each individual arrow in the drawings represents a single pulse-echo sequence (or transmit/receive event).

Interleaved with the frames 110 of the first imaging mode (e.g., with each 3D frame acquired by Seq. 1) are individual 2D frames 120, each of which is produced by another sequence, Seq. 2. In this example, Seq. 2 is composed of 11 individual transmit/receive events, each configured to acquire a scan line 122 in a particular azimuthal plane to produce the set of scan lines 122 corresponding to a single scan plane of the 2D image. As with Seq. 1, the number of individual scan lines and corresponding transmit/receive events, illustrated by the individual arrows and shown here for illustration only as numbering 11, would likely be much greater in a real life application, e.g., ranging anywhere from about 80 to about 200 or more lines. In embodiments, the scan lines that form an image (e.g., a 2D or 3D image) are acquired by selectively activating one or more elements of the transducer array in the appropriate pattern, the selective activation (or firing) of the transducer elements occurring responsive to a controller (e.g., transmit/receive controller) of the ultrasound scanner. A pattern like the exemplary pattern shown in FIG. 1 may be the only pattern for combining imaging in two particular modes in existing systems. This single pattern may be pre-programmed in the system and would be invoked/applied any time that the user wishes to concurrently image in a particular combination of imaging modes. That is, in existing systems, no mechanism exists for prioritizing one mode over the other and/or selectively increasing the frame rate of one more over the other.

In accordance with the present invention, described here are systems and methods for enabling the selective prioritization of one of a plurality of imagining modes in a multi-mode imaging operation. In some embodiments, the system is equipped with one or more user interface elements that enable the operator to adjust the relative priority of imaging modes, such as by increasing or setting the priority of one mode over that of other modes in a multi-mode operation. In some embodiments. 25 increasing the priority of one imaging mode causes the temporal resolution (e.g., frame rate) of that mode to increase relative to the temporal resolution of other ones of the multiple imaging modes. In some embodiments, the systems is additionally or alternatively configured to apply situational priority such that it automatically prioritizes (e.g., by increasing the frame rate of) one mode over the others, for example based on a given condition. A system according to the present disclosure may be configured to apply, responsive to user input (e.g., a priority setting) or situational condition, an interleave pattern which is selected from a plurality of pre-defined interleave patterns or is determined by the system in accordance with a set of predefined rules.

Figure 2:
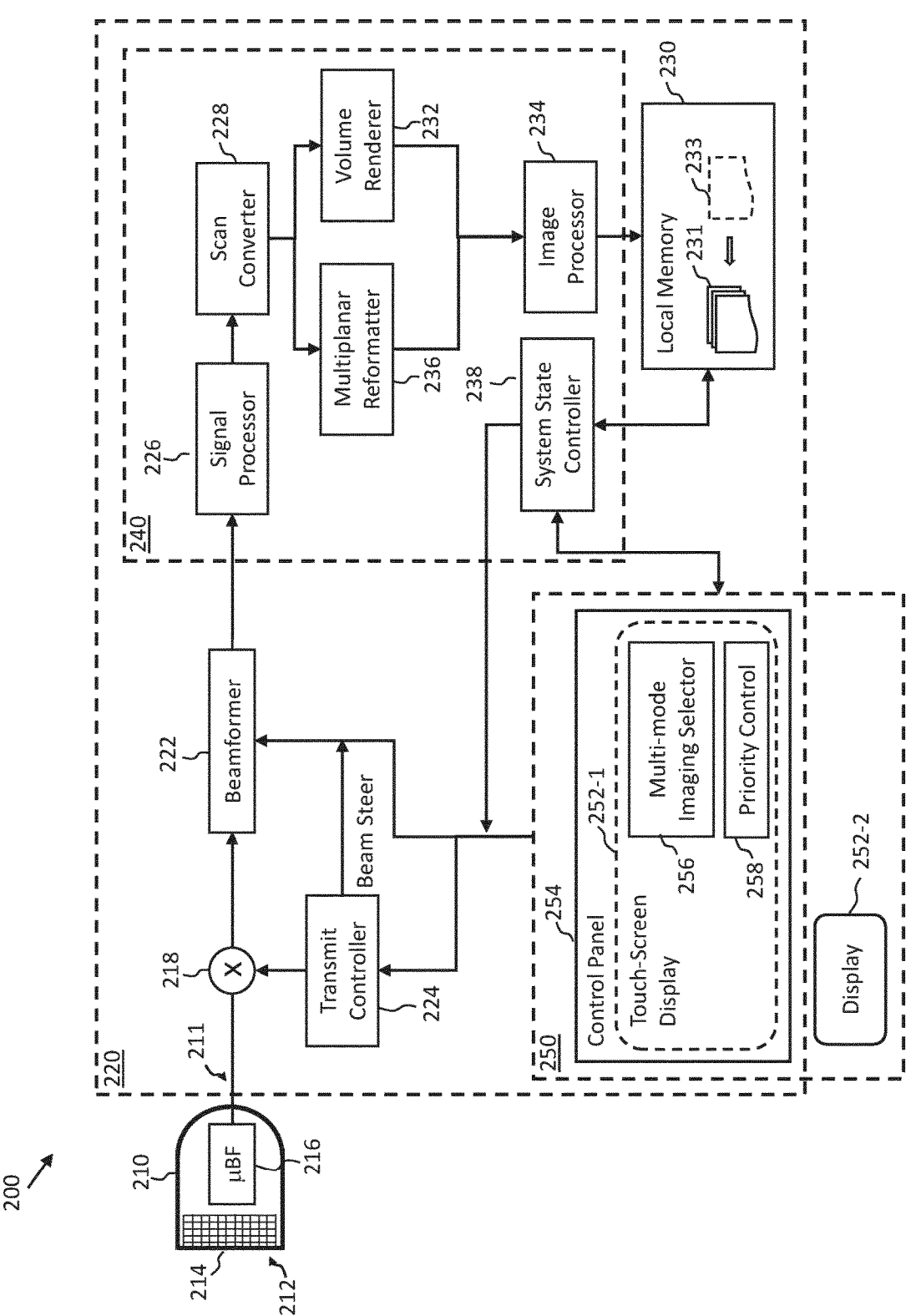
FIG. 2 is a block diagram of an ultrasound imaging system arranged to image a target medium concurrently in multiple imaging modes, in accordance with the present invention.

FIG. 2 shows a block diagram of a system 200, arranged to perform ultrasound imaging according to aspects of the present disclosure. The system 200 is configured for ultrasonically scanning an area or volume of a patient's body, and may thus be referred to as an ultrasound scanner. The system 200 includes electronic components which are configured to cause the transmission and reception of ultrasound signals and to perform signal and image processing for generating ultrasound images therefrom. At least some of the electronic components of the system 200 are be provided in a main processing portion 220 of the ultrasound scanner, also referred to as base or host 220 of the ultrasound scanner. During use, the base 220 is communicatively connected to an ultrasound probe 210 via communication link 211, which may be implemented by a wired connection (e.g., serial. USB or other cable) or a wireless link. The system 200 includes a processor 240, which performs functions (e.g., signal and image processing of acquired data) associated with generating ultrasound images according to the present disclosure. While referring herein to a processor, it will be understood that the functionality of processor 240 may be implemented by a single or a plurality of individual components (e.g., a plurality of individual processing units) operatively configured to perform the functions associated with processor 240. For example, processor 240 may be implemented by one or a plurality of general purpose processors and/or microprocessors configured to perform the tasks described herein, by any suitable combination of application specific circuits (ASICs), one or more graphical processing units (GPUs), one or more field programmable gate arrays (FPGAs) or any suitable combinations thereof.

The system 200 also includes a user interface 250 which enables a user to control certain operations of the ultrasound system 200. The user interface 250 includes a control panel 254, which may include any suitable combination of mechanical or hard controls (e.g., buttons, switches, dials, sliders, encoders, a trackball, etc.) and/or soft controls, such as a touch pad and various graphical user interface (GUI) elements that may include any suitable combination of menus, selectable icons, text-input fields, and various other controls or widgets, provided on a touch-sensitive display (or touch screen) 252-1. The user interface 250 may include other well-known input and output devices. For example, the user interface 250 may optionally include audio feedback device(s) (e.g., alarms or buzzers), voice command receivers, which can receive and recognize a variety of auditory inputs, and tactile input and/or output devices (e.g., a vibrator arranged on a handheld probe for tactile feedback to the user). The user interface 250 may include any suitable number of displays, such as one or more passive displays 252-2 (e.g., for displaying ultrasound images) and/or one or more touch screens 252-1, which may form part of the control panel 254 of the system 200. The one or more displays of the system may be implemented using a variety of known display technologies, such as LCD. LED. OLED, or plasma display technology The system 200 also includes local memory 230, which may be implemented by one or more memory devices arranged in any suitable combination. The memory 230 stores information necessary for the operation of the system 200. For example, the memory 230 may store executable instructions that configures the processor 240 to execute one or more of the functions associated therewith. The memory 230 may also store interleave patterns for interleaving the acquisition sequences of multiple imaging modes during a multi-mode imaging operation. In some embodiments, the memory 230 stores predefined rules for determining the interleave pattern based on the specific priority setting. e.g., specified by the user.

As previously noted, the system 200 is configured to communicatively couple to a probe 210, which includes an ultrasound transducer 212, optionally a beamformer (e.g., microbeamformer 216), one or more analog and digital components (e.g., for converting analog signals to digital signals and vice versa), and a communication interface (not shown) for communicating, via the communication link 211, signals between the transducer 212 and the base 220. The probe 210 may be in any suitable form for imaging various body parts of a patient, e.g., the heart, vasculature, abdomen etc., while positioned inside or outside of the patient's body. In an embodiment, the probe 210 is an external ultrasound imaging device including a rigid housing arranged for handheld operation by a user (e.g., a sonographer), referred to herein as a handheld probe. The probe's transducer 212 may be arranged to obtain ultrasound signals while the user grasps the housing of the probe 210 such that the transducer 212 is positioned adjacent to and/or in contact with a patient's skin. In other embodiments, the probe 210 is provide in a bendable form factor. For example, the probe may include one or more bendable portions (e.g., transducers patches movably coupled together) allowing it to be positioned and held conformally against the patient's body, and may thus be referred to flexible or conformal ultrasound probe. In some embodiments, the probe 210 is arranged to detect and record ultrasound echo signals reflected from the patients's anatomy within the patient's body while the probe 210 remains positioned outside of the patient's body. In other embodiments, the probe 210 may be in the form of a catheter, an intravascular ultrasound (IVUS) catheter, an intracardiac echocardiography (ICE) catheter, a transesophageal echocardiography (TEE) probe, a transthoracic echocardiography (TTE) probe, an endo-cavity probe or any other form factor suitable for internal application in the patient's body.

The ultrasound transducer 212 in the example in FIG. 1 is shown as a transducer array 214, which is configured to transmit ultrasound signals (e.g., beams, waves) into a target region (e.g., into the patient's body) and receive echoes (e.g., received ultrasound signals) responsive to the transmitted ultrasound signals from the target region. The probe's transducer may include any suitable array of transducer elements which can be selectively activated to transmit and receive the ultrasound signals for generating images of the anatomy. A variety of transducer arrays may be used, e.g., linear arrays, curved arrays, or phased arrays. The transducer array 214, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction. In some examples, the transducer array 214 may be coupled to a microbeamformer 216, which may be located in the ultrasound probe 210, and which may control the transmission and reception of signals by the transducer elements in the array 214. In some examples, the microbeamformer 216 may control the transmission and reception of signals by active elements in the array 214 (e.g., an active subset of elements of the array that define the active aperture at any given time). In some examples, the microbeamformer 216 may be coupled, e.g., by a probe cable or wirelessly, to a transmit/receive (T/R) switch 218, which switches between transmission and reception and protects the main beamformer 222 from high energy transmit signals. In some examples, for example in portable ultrasound systems, the T/R switch 218 and other elements of the system 200 that are shown in FIG. 1 as located in the base 220, may instead be included in the ultrasound probe 210.

The transmission of ultrasonic signals from the transducer array 214, e.g., optionally under the control of the microbeamformer 216, may be directed by a transmit controller 224, which may be coupled to the T/R switch 218 and the main beamformer 222. The transmit controller 224 may control characteristics of the ultrasound signals transmitted by the transducer array 214, for example, amplitude, phase, and/or polarity of the waveform. The transmission of signals (i.e. acoustic energy) from the transducer array 214, under the control of transmit controller 224, occurs in accordance with acoustic settings, also referred to as imaging or acquisition settings, which may be manually controlled by the user (e.g., set via the user interface 250) and/or at least partially automatically controlled by a processor of the system 200. The transmit controller 224 may also control the direction in which beams are steered. Beams may be steered straight ahead from (orthogonal to) the transducer array 214, or at different angles for a wider field of view. The transmit controller 224 may be coupled to the user interface 250, via which the system 200 receives user input. For example, the user may select whether transmit controller 224 causes the transducer array 214 to operate in a harmonic imaging mode, fundamental imaging mode, Doppler imaging mode, or a combination of imaging modes (e.g., interleaving different imaging modes). Furthermore, when imaging in two or more modes concurrently (i.e. multi-mode imaging), the system 200 may be configured to prioritize one of the multiple imaging modes over the others (e.g., responsive to user input via the user interface 250 and/or based on the occurrence of a condition) and the transmit controller 224 may, responsively, apply an interleave pattern, selected or particularly defined based on the specified priority, such that the transmit/receive events of the different imaging modes are interleaved in accordance with the interleave patterns provided to the transmit controller 224.

In some examples, the partially beamformed signals produced by the microbeamformer 216 may be coupled to the main beamformer 222 where partially beamformed signals from individual patches of transducer elements may be combined into a fully beamformed signal. In some examples, microbeamformer 216 can be omitted, and the transducer array 214 may be under the control of the main beamformer 222, which can then perform all beamforming of signals. The beamformed signals are coupled to signal processing circuitry (e.g., to the processor(s) 240) configured to produce ultrasound images of the patient's anatomy from the beamformed signals, in some case live or in real-time as the ultrasound signals are being acquired by and while scanning the patient.

The signal processing circuitry (e.g., processor(s) 240) of the host 220 includes a signal processor 226. The signal processor 226 may process the received beamformed signal in various ways. e.g., including any suitable combination of bandpass filtering, decimation, I and Q component separation, and harmonic signal separation, to generate image data. The processing of signals performed by signal processor 226 may be different based, at least in part, on the imaging mode in which the system 200 is set to acquire signals. As described herein, the system 200 is operable to intermittently switch between different imaging modes, e.g., responsive to control from the transmit controller 224, to acquire signals for each of the different imaging modes when imaging concurrently in multiple modes. For example, the system 200 may be configured to image the patient's anatomy in any one of a plurality of different imaging modes, and in some cases, responsive to user input, in a plurality of imaging modes such as, but not limited to, B-mode, M-mode, Pulsed-Wave/Spectral Doppler, Power/Color Doppler, elastography, contrast-enhanced ultrasound (CEUS) imaging, microflow imaging (MFI) and others. In some embodiments, e.g., such as during B-mode imaging, the signal processor 226 may perform I/Q demodulation on the signal and then perform amplitude detection to extract amplitude data (e.g., A-lines) that can be arranged into a B-mode image. In the case of Doppler imaging, the signal processor 226 may perform additional or different combinations of filtering, spectrum analysis and/or flow estimation (e.g., Doppler or frequency shift estimation) to obtain suitable data for generating the selected type of images. In some embodiments, the system 200 is configured to perform live multi-mode imaging in which the system acquires ultrasound signals for two or more different imaging modes at the same time, such as by interleaving the acquisitions associated with each of the different modes. In such instances, acquired signal(s) associated with a first imaging mode (e.g., B-mode) may be processed by the signal processor 226 in a manner suitable for generated B-mode image data, the acquired signal(s) associated with a second imaging mode (e.g., color Doppler) are processed by the signal processor 226 in a manner suitable for generated color Doppler image data, and so on.

Following processing by signal processor 226, the image data is coupled to a scan converter 228 and/or a multiplanar reformatter 236. The scan converter 228 may be configured to arrange the data from the spatial relationship in which they were received to a desired image format so that the image data is presented on the display in the intended geometric format. For instance, data collected by a linear array transducer would be arranged into a rectangle or a trapezoid, whereas image data collected by a sector probe would be represent as a sector of a circle. As such, scan converter 228 is configured to arrange the image data from the spatial relationship in which they were received to the appropriate image format. The image data may be arranged by scan converter 228 into the appropriate two dimensional (2D) format (e.g., 2D sector format), or three dimensional (3D) format (e.g., a pyramidal or otherwise shaped format). The processor(s) may implement a multiplanar reformatter 236, which is configured to perform multiplanar reconstruction, e.g. by arranging data received from points in a common plane in a volumetric region into an image of that plane or slice, for example as described in U.S. Pat. No. 6,443,896 (Detmer). The scan converter 228 and multiplanar reformatter 236 may be implemented as one or more processors in some embodiments. A volume renderer 232 may generate an image (also referred to as a projection, render, or rendering) of the 3D dataset as viewed from a given reference point, e.g., as described in U.S. Pat. No. 6,530,885 (Entrekin et al.). The volume renderer 232 may be implemented by one or more processors. The volume renderer 232 may generate a render, such as a positive render or a negative render, by any known or future known technique such as surface rendering and maximum intensity rendering. The image data may be further enhanced, e.g., by image processor 234, through speckle reduction, signal compounding, spatial and temporal denoising, and contrast and intensity optimization. Numerous other signal and image processing techniques for generating images for various imaging modes have been developed and are well known and thus outside of the scope of the present invention. Thus for conciseness, these various techniques are not detailed herein and it will be understood that any suitable technique(s), currently know or later developed, for processing the acquired ultrasound signals to produce images for one or more desired imaging modes can be used without departing from the scope of the present disclosure. The image frames associated with each imaging mode may be stored locally, e.g., in a corresponding memory portion of local memory 230. Local memory 230 may be implemented as any suitable non-transitory computer readable medium (e.g., flash drive, disk drive). In some examples, local memory 230 may include multiple memories, which may be the same or of different type. For example, local memory 230 may include a dynamic random access memory (DRAM) and a flash memory. The image frames from memory 230 may be coupled, via system state controller 238 to the user interface 250. e.g., to one or more of the displays for presenting the acquired images in real time (or live) as they are being acquired.

In accordance with the principles of the present disclosure, the system 200 is configured to be operated in a multi-mode imaging state in which the system concurrently acquires signals for two or more imaging modes for generating and/or displaying real-time images associated with multiple modes. The system 200 is configured to perform multi-mode imaging upon selection of a particular combined imaging option (e.g., CEUS, Color Doppler which combines flow and tissue imaging, elastography which combines tissue and stiffness measurements, etc., where any of the two or more modes combined may be imaged in 2D or 3D), via the user interface (e.g., via a first user control 256, which may be implemented by one or a set of soft controls or buttons, shown collective in FIG. 2 as "Multi-mode Imaging Selector" control 256). Furthermore, the system 200 is configured to selectively prioritize one of the plurality of imaging modes during such a multi-mode imaging operation, resulting in the increase of the frame rate of the prioritized mode typically at the expense of the frame rate(s) of the remaining modes. The system 200 may prioritize a particular mode over others based on a specific setting or based on a condition, each of which may be specified or triggered by a second user control 258, which may be implemented by one or a set of soft controls or buttons, shown collective in FIG. 2 as "Priority Control" control 258. In some embodiments the second user control 258 may be configured to enable the user to manually adjust the priority of the modes or it may control, such as via a timers, a conditional change to the priority of the modes, as described further below. In some embodiments the first user control 256 and the second user control 258 may be presented on the same user interface screen. In other embodiments, the first user control 256 and the second user control 258 may be presented one after the other, on different screens of the user interface. For example, the selection of multi-mode imaging may occur first, and a suitable second user control 258 may be displayed next and based on the selection made via the first user control 256.

Figure 3:
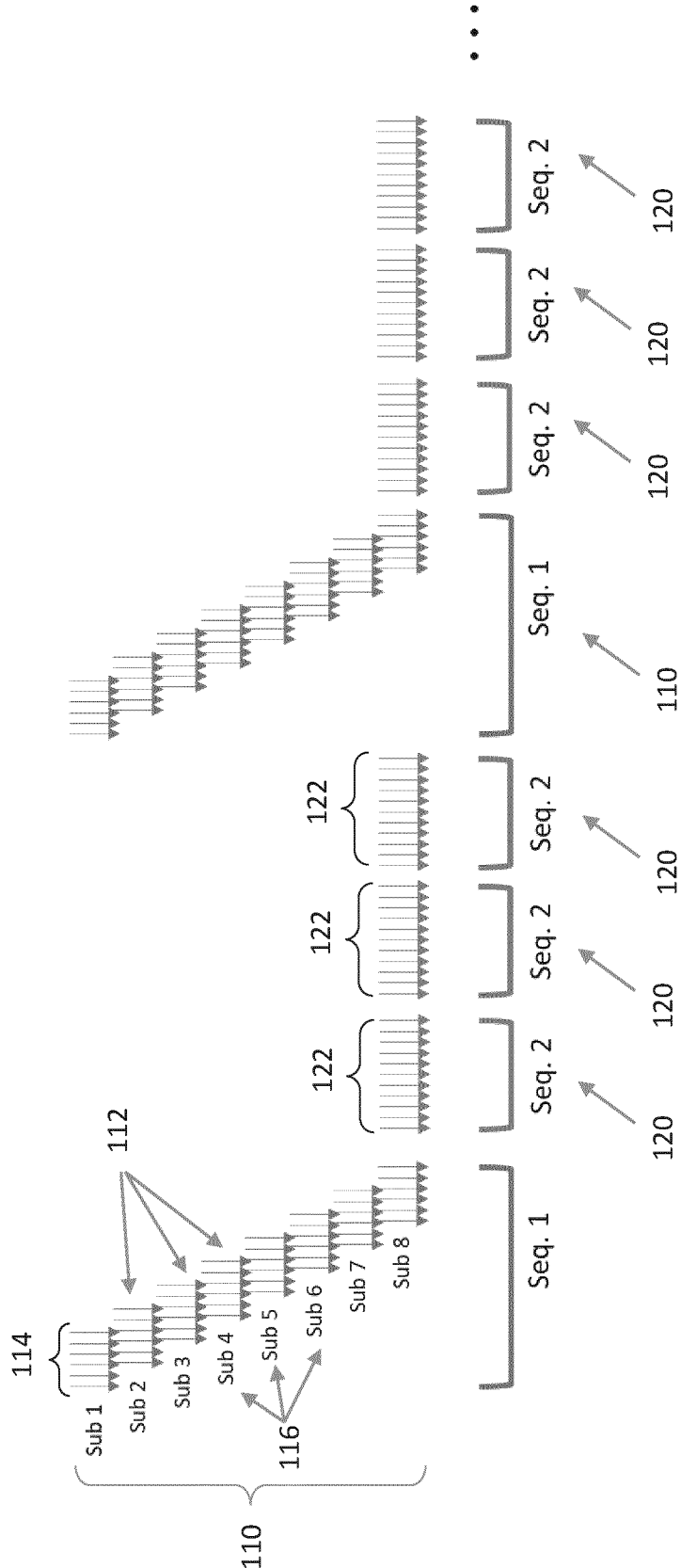
FIG. 3 shows an interleave pattern for concurrently imaging in two modes as in the example in FIG. 1, but which increases the frame rate of the 2D imaging mode, as compared to the example of FIG. 1.

FIG. 3 shows an example interleave pattern in which one or more full 2D frames are added for each 3D frame responsive to increased priority of the second mode. Continuing here with the example scenario of contrast enhanced ultrasound imaging (CEUS), the system 200 may be controlled to prioritize (e.g., responsive to user input or based on conditional change in priority) the B-mode (or tissue) imaging mode represented by Seq. 2. As a result, additional 2D (e.g., tissue) frames, here tissue frames, are acquired for each 3D (e.g., contrast) frame. In the specific example in FIG. 3, two additional 2D frames are added for each 3D frame. However, it will be understood that in other examples a different (fewer or greater) number of frames of frames may be added, which may depend upon the specific relative priority to which the system is set. Similar to the example in FIG. 1, each arrow in the collection of arrows 114 corresponds to a transmit/receive event, e.g., associated with a scan line, of a 3D frame of the first imaging mode (e.g., represented by Seq. 1), and each grouping of transmit/receive events associated with a given sub-sequence 116 (e.g., Sub 1-8) from the larger 3D frame sequence (Seq. 1) produces a group of scan lines, e.g., a different scan plane of the 3D volume, which collectively produce one 3D frame 110. In FIG. 3, the acquisitions associated with two temporally consecutive 3D frames are shown, and three 2D frames 120 are interleaved, in this case following the completion of a 3D frame, after each of the 3D frames. As in the example of FIG. 1, each 2D frame is acquired by the same sequence of transmit/receive events 122, which is initiated after the completion of the 3D frame and repeated multiple (here 3) times in succession before the initiation of the next 3D frame. As can be appreciated, the interleave pattern in FIG. 3 allows for the frame rate of one mode (here the second mode) to be increased while preserving a precisely timed ensembles of pulses in the 3D mode sequence, which may be critical for certain imaging modes (e.g., Doppler imaging), where maintaining the sequential transmission of all acquisitions for the frame may be essential for accurately measuring the Doppler shift. However, in some cases, preserving the full sequence of one mode while adding additional frames of the other mode may produce unacceptable discontinuities in some of the modes, such as motion artifacts or frame stutter. These effects may be mitigated via frame interpolation algorithms or artifact correction algorithms (motion correction, jailbar softening, etc.), or through the selection of a different interleave pattern if it is acceptable for the particular combination of imaging modes.

Figure 4:
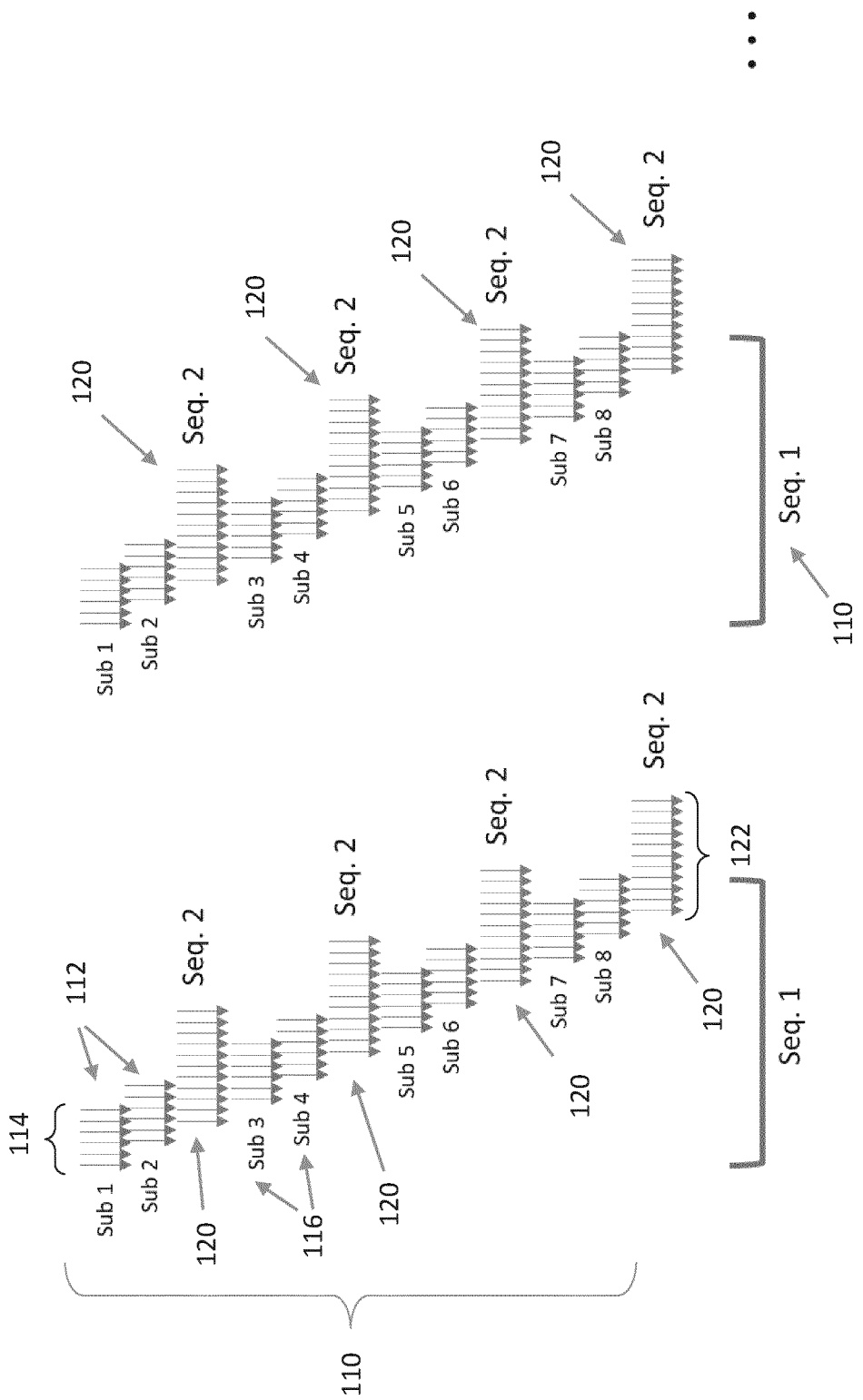
FIG. 4 shows another interleave pattern that increases the frame rate of the 2D imaging mode, when compared to the example of FIG. 1, in an multi-mode imaging operation.

One such alternative interleave pattern which increases the frame rate of one of the multiple modes without as perceivable discontinuity in the other mode is shown in FIG. 4. In the example in FIG. 4, the pattern interleaves the acquisitions for each of a plurality of 2D frames with the acquisitions of a single 3D frame. In other words, in this example, instead of waiting to complete a full 3D frame before switching to the second imaging mode, the system switches between the first and second modes, while still capturing image data associated with a single 3D frame. In the specific example in FIG. 4, the system is set to acquire one or more, but less than all, planes 112 of a 3D frame, interspersed between which are one or more 2D frames 120. Here, a single 2D frame 120 is interleaved between the planes 112 of the 3D frames, but it will be understood that in other examples, more than one 2D frame 120 may be acquired in between the planes 112 of the 3D frame. Also, shown here is that the 2D frames 120 are interleaved at every two planes 112 of the 3D frame, but in other examples, the 2D frames may be interleaved differently such as alternated with each individual plane 112 or interleaved between more than 2 (e.g., every 4 planes, or in some cases fewer or greater number of planes, depending on the total number of planes that compose the full 3D frame). Ideally, when applying this type of interleave pattern, which intersperses the acquisitions of one imaging modes within the frame of the other acquisition mode, the 3D volume should be split into a suitable (e.g., even) number of planes to allow for the interleaving of the other mode(s) frames therebetween. As previously noted, the exact configuration of the interleave pattern (e.g., how many 2D frame are interleaved and between how many planes of the 3D mode they are interleaved in) may depend upon the priority setting. In yet further examples, the interleaving techniques in FIGS. 3 and 4 may be used in combination, resulting in an interleave pattern in which 2D frames are acquired, fully or partially, during the acquisition of a single 3D frame and additional one or more 2D frames are also added between the 3D frames. While the interleave patterns in FIGS. 1, 3, and 4 have been described with reference to CEUS, it will be understood that these interleave patterns may apply to other imaging mode combinations. That is, the first imaging mode may be any 3D imaging mode, such B-mode (i.e., volumetric tissue imaging). Color Doppler, elastography, etc., and similarly the second imaging mode may be any 2D imaging mode (e.g., B-mode, Doppler, etc.).

To effect the prioritization of at least one imaging mode over other imaging mode(s) in a multi-mode imaging operation, and referring back to FIG. 2, the system 200 includes a memory, which may store a plurality of interleave patterns 231, and further includes one or more user controls (e.g., priority control 258) provided by the user interface 250 to enable the prioritization (e.g., responsive to user input) of at least one of the plurality of modes selected by the Multimode Imaging Selector control 256. In some embodiments, the memory 230 may additionally or alternatively store a set of rules 233 for determining an appropriate interleave pattern 231 based on the user-specified or system-controlled priority setting. A processor 240 (e.g., system state controller 238) may receive and interpret the priority setting of the imaging modes. The priority of the imaging modes may be set by the user, e.g., at the start of the exam, and/or it may be changed (e.g., responsive to the user or based on the occurrence of a condition detected by the system) during an exam, as will be further described. The processor 240 (e.g., system state controller 238) receives the priority setting and selects and/or defines the appropriate interleave pattern based on the set/adjusted priority. As previously noted, the user interface 250 of the system 200 may be implemented using any suitable combination of hard controls (e.g., buttons, switches, sliders, dials, a trackball, etc. provided on control panel 254) and soft controls (e.g., one or more GUI elements provided on a touch screen 252-1), one or more of which may be specifically configured to enable the operator to modify the priority of an imaging mode during a multimode imaging operation.

Various examples user interface (UI) elements configured to enable the operator to modify the priority of an imaging mode during a multi-mode imaging operation are illustrated and described with reference to FIGS. 5-13, any of the UI elements described with reference to FIGS. 5-13 may alone or in any suitable combination be used to implement priority control 258, to enable the user-control or conditional adjustment of priority between the multiple modes. While one or more of the examples that follow are described as GUI elements of a touch screen interface, the GUI elements of these examples may be equivalently implemented by hard controls of the control panel 254 without departing from the scope of the present invention and vice versa.

Figures 5, 6, 7, 8:
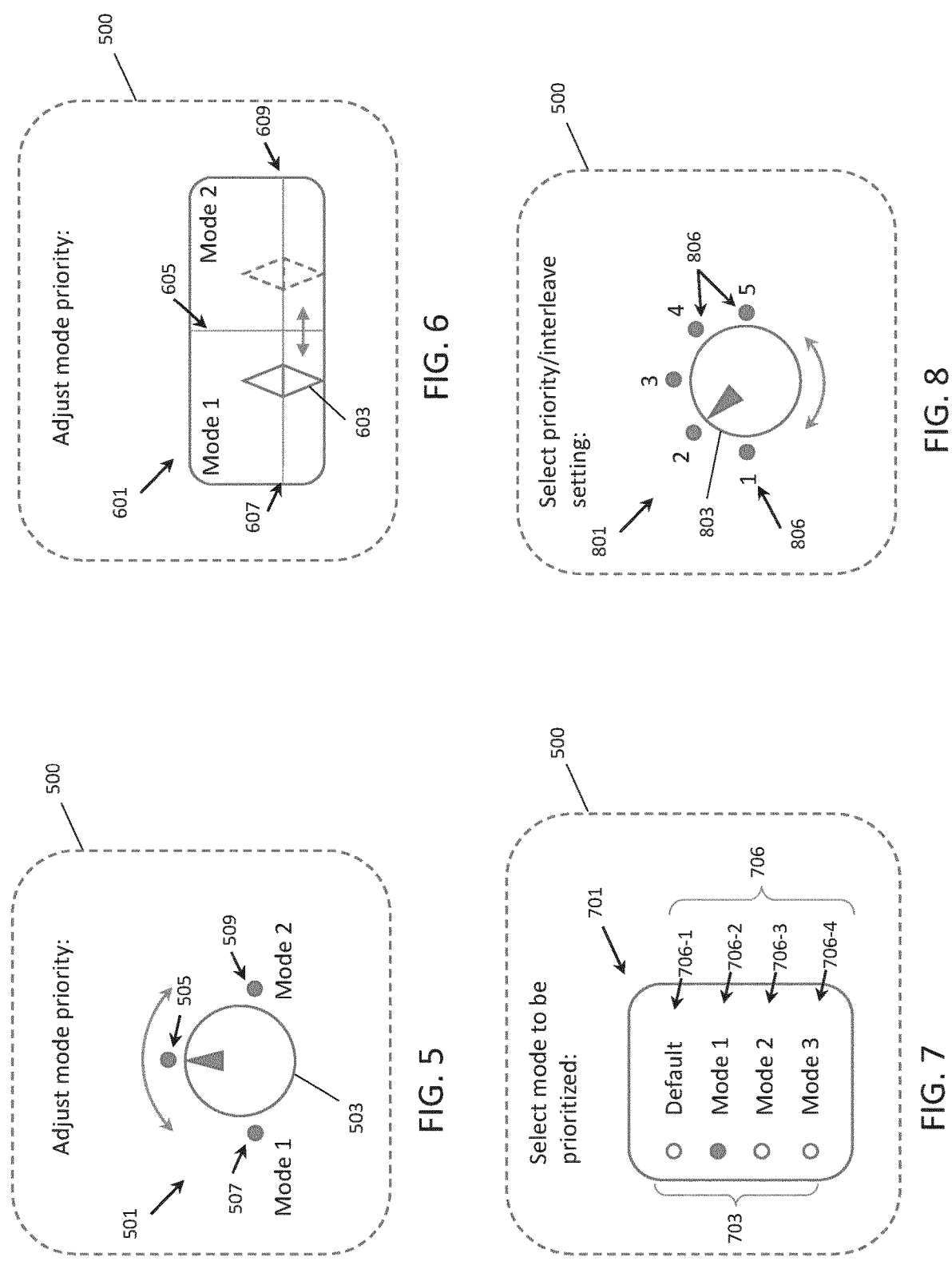
FIGS. 5-12 shows various examples of user controls for selectively prioritizing one of the imaging modes over other ones of the imaging modes.

FIG. 5 shows an example of a user interface (UI) element 501, which may be implemented as a hard control (e.g., a mechanical dial) or a soft control (e.g., a GUI dial widget) on a control panel 500 (e.g., console panel or touch-screen panel, respectively). The UI element 501 of this example is in the form of a dial 503 which can be rotated away from the balanced setting 505 toward a first priority setting 507 which changes the priority balance in favor of prioritizing Mode 1 or toward a second priority setting 509 which changes the priority balance in favor of prioritizing Mode 2. The first and second modes may be, and thus consequently the first and second settings may be associated with, any two modes that are being imaged concurrently (e.g., a Color Doppler/B-mode imaging. CEUS (either 2D or 3D), elastography with tissue, MFI, etc.). The dial control of this example may be configured to be continuously or smoothly rotated for adjusting the priority balance of two imaging modes, with the balanced or neutral priority setting 505 corresponding to a setting in which the two modes are prioritized equally (e.g., applying an interleave pattern for example as shown in FIG. 1 or other predefined interleave pattern which achieves a substantially evenly prioritized frame rates for both modes).

In other examples, the dial control may be "slotted" or detented into a plurality of discrete settings, which may be configured for incrementally adjusting the priority balance to any of the available priority settings, with settings one side of the balanced setting corresponding to increasing priority towards one of the two modes and settings on the opposite side of the balanced setting corresponding to increasing priority towards the other one of the two modes. The system 200 may select or determine an appropriate interleave pattern that corresponds to the specified priority setting. For example, setting the dial to the second (Mode 2) setting 509, may result in applying an interleave pattern producing the highest possible frame rate for the second mode, while sacrificing temporal resolution of the first mode. Similarly, shifting the dial towards the first (Mode 1) setting 507, increases the frame rate of the first imaging mode at the expense of the second imaging mode.

A similar result may be achieved with a user interface (UI) element 601 according to the example in FIG. 6. Here, the UI element 601 is implemented by a slider control 603, which can be shifted, incrementally or smoothly/gradually, to a plurality of priority settings including a balanced setting 605, a first priority setting 607, which prioritizes Mode 1 over Mode 2, and a second priority setting 609, which prioritized Mode 2 over Mode 1. As with the prior example, the slider control 603 may be implemented by a hard control (e.g., a mechanical slider) or a soft control (e.g., a GUI slider widget) on control panel 500 (e.g., console panel or touch-screen panel, respectively). In some embodiments, the type of control provided by the system (e.g., the type of GUI control displayed on a touch screen interface) may depend upon the specific combination and/or number of imaging modes in which the user selects to concurrently image in.

Figures 9, 10, 11, 12:
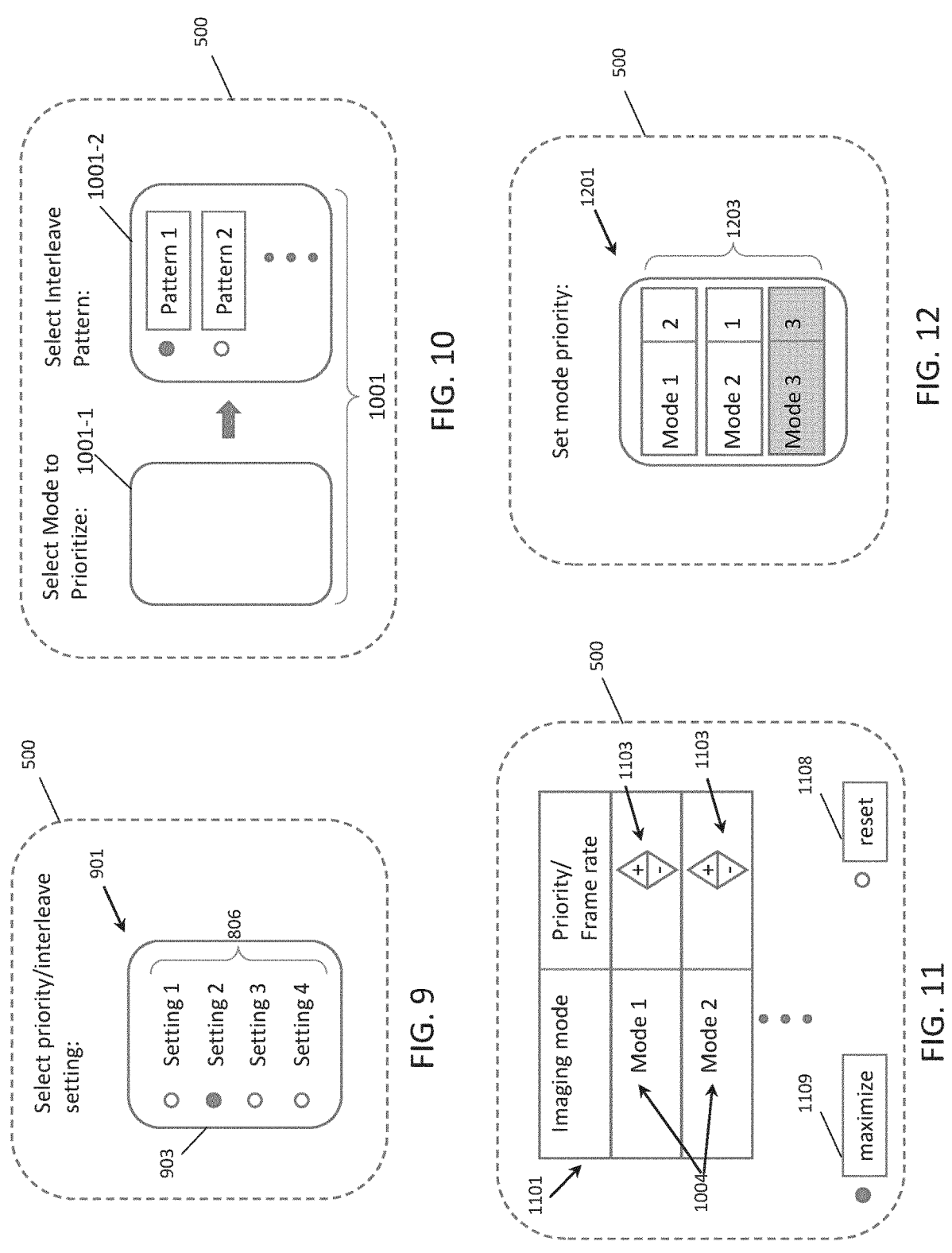

In some embodiments, the priority control is implemented by a UI element that has a plurality of discrete settings, only one of which is selectable at any given time. This can be implemented, for example, by any suitable hard control(s) such as buttons or switches, such as where pushing one button/switch disengages the other button(s)/switch(es), or by a multi-way switch (e.g., a two-way or three-way switch) or by any suitable soft control(s), for example radio buttons or other suitable GUI widgets that, upon selection of an option, deselect the other available options. Each of the discrete setting may correspond to various options, for example to a particular mode to be prioritized, to one of a plurality of different priority combinations that provide a different priority balance among multiple imaging modes, a particular desired frame rate increase, etc., or combinations thereof. Some non-limiting examples of UI elements that can be used to implement such a UI element are shown in FIG. 7-9. In the example in FIG. 7, the UI element 701 is implemented by a set radio buttons 703, each button being associated with a unique setting 706, showing here 4 settings but understanding that in other examples a different number of setting may be included. The individual settings (e.g., settings 706-2 through 706-4 of the UI element 701 correspond to one of the plurality of imaging modes in which the system is set to concurrently image. The UI element 701 may include a first setting 706-1 which may correspond to a default (or balanced) mode in which all of the imaging modes are substantially equally prioritized. Each of the remaining individual settings (e.g., settings 706-2 through 706-4) may correspond to a respective one of the plurality of imaging modes in which the system is set to concurrently image. As noted previously, the number of modes may vary based upon the user's selection (e.g., based on input received via the user control shown as Multi-mode Imaging Selector control 256 in FIG. 2), and thus in some examples the number of settings provided by UI element 701 may be smaller or greater than the specific illustrated example in FIG. 7.

Another example of this type of control is shown in FIG. 8, where the UI element 801 is implemented by a dial 803 (e.g., either a hard/mechanical dial or a GUI dial) associated with a plurality of discrete settings 806. The settings 806 in this example may be the same as in the example in FIG. 8. In other embodiments, each setting may correspond to one of a plurality of different options, each of which corresponds to a different combination of priority and interleave type. For example, in 3D contrast/tissue imaging, setting 1 may correspond to: prioritize B-mode, interleave type 1 (e.g., as shown in FIG. 3), setting 2 may correspond to: prioritize B-mode, interleave type 2 (e.g., as shown in FIG. 4), setting 3 may correspond to: priority balanced, interleave type 1 (e.g., as shown in FIG. 1), and settings 4 and 5 may correspond to prioritizing contrast each in combination with two different types of interleave patterns. Alternatively, setting 4 may provide an alternative interleave pattern for a balanced priority and setting 5 may be the only option for prioritizing the contrast mode. Of course, in the case of a different a multi-mode imaging operation when different modes are combined, the settings would correspond to different options relevant to the selected multi-mode imaging. The concept of distinct settings shown in the example in FIG. 8 may also be implemented by a radio-button 903 style GUI element 901 as shown in FIG. 9, or any other suitable user control.

In some embodiments, the priority control may be configured to enable the user to separately select a mode to be prioritized and also to select one from among a plurality of available interleave patterns that prioritize the selected mode. This may be useful in cases where more than one interleave patterns are available in memory, which can be used to prioritize a particular one of the different modes. One example of such a user control is shown in FIG. 10. The UI element 1001 that implements the priority control has two components, a first control 1001-1 configured to allow the user to selectively prioritize one of the plurality of imaging modes. The first control 1001-1 may be implemented using any of the examples herein, such as the UI elements shown in FIGS. 5-7. In some examples the selection of a mode to be prioritized in this or other embodiments, may be via a selectable icon where each icon includes a graphic or thumbnail representative of the corresponding mode. Depending on the selection made via the first control 1001-1, the UI element 1001 may display a second control 1001-2 which presents the available interleave pattern options for the selected mode to be prioritized. In some cases, such as when a balanced option is selected via the first control 1001-1 or when the prioritized mode is not associated with multiple interleave patterns the second control 1001-2 may not be displayed and the system will then continue on with other settings and/or proceed to other steps in the exam. In scenarios in which a second control 1001-2 is presented, the second control 1001-2 may be similarly implemented by any suitable selector-type control that allows the user to select only one of a plurality of available options. This selector may be in the form of a dial with discrete settings, radio buttons, selectable icon with appropriate graphic (e.g., one that illustrates or otherwise provides indication of the corresponding pattern), etc. In other embodiments, the appropriate interleave pattern for a particular priority setting may be selected by the system based on the programming of processor 240 and may depend primarily on the imaging modes combination. In some modes, such Doppler imaging, there is a very high priority on preserving a precisely timed ensemble of pulses in sequence in order to accurately measure displacement. In such cases, it would be important to perform all of the transmit/receives for that mode before switching to the other. In other modes, such as contrast, there may be more flexibility in this regard, and in such instances, it may be acceptable to alternate between the different imaging modes and disrupt the contrast sequence to capture a piece of or a full frame of the other mode at a similar spatial/temporal point. Thus, for scenarios of this latter type, various user controls that either provide explicit control to the user to select the interleave type, as in the example in FIG. 10, or which provide multiple settings each associated with a different interleave type may be used.

FIG. 11 shows yet another example for implementing the priority control. In this example, the system generates and displays a UI element 1101 which list the plurality of modes 1004 associated with the selected combined/multi-mode imaging state, and an up/down arrow control 1103 for each of the plurality of modes 1104. The user can increase the priority of one mode by clicking on the up arrow of that mode. Consequently, if only two modes are being combined, the up/down arrow for the other mode may be disabled (and the corresponding row grayed out for visual indication of this) in response to adjusting the other mode. The UI element 1101 may include a reset button 1108 for resetting the UI element 1101 to the default (e.g., balanced) state and re-activating both up/down arrows, in the event the user wishes to prioritized another mode. If more than two modes are being combined, the up/down arrows for all modes remain active until only one mode remains to be adjusted, in which case that mode is deactivated, as the priority setting for that mode will depend upon the adjustments made to the other modes. Another example of a user control for similarly adjusting the priority of one or more of the plurality of modes is shown in FIG. 12, which instead uses text input fields 1203 that receive a text input specifying the priority of the different modes. The UI element 1201 in the example of FIG. 12 includes three text input fields 1203, one associated with each of three different imaging modes, however it will be understood that in other examples fewer or greater number of text input fields 1203 may be provided depending on the number of modes being combined. Similarly here, the user may specify the first, and optionally second and/or third if more than two modes are combined, and the last input field is grayed out and automatically set to the last priority upon receipt of input in all but one of the text input fields.

In some embodiments, it may be desirable to provide a control enabling the user to decrease the frame-rate rather of one or both modes rather than running at a maximum condition. This could be useful either for reducing data size (which would be generally applicable to any imaging), or for reducing some other effect (e.g., thermal heating at the probe surface caused by repetitive pulsing, or something the destroying of contrast agent in circulation through repetitive pulsing) that may result when running at a "maximum" rate. While the system may be equipped with other mechanisms to control this (e.g. user interface buttons to increase dead time between pulses), this control may be further enhanced and/or wrapped together in a frame rate control similar to the example shown in FIG. 11. Therefore, in some embodiments, the priority control may be used not only to enhance temporal resolution but additionally or alternatively in the reverse, e.g., to control negative effects of operating one or all modes at the maximum rate. In some such embodiments. UI element 1101 may additionally include a maximize option 1109, which may be selected by default and may be de-selectable by the user. When option 1109 is selected, the system automatically calculates the frame rates of lower priority modes to operate at the maximum rate for the combined modes. When option 1109 is de-selected, the user is able to intentionally reduce the frame rate of one or more modes for the enhanced control of "negative" effects that may result from running at "maximum" rate.

Figure 13:
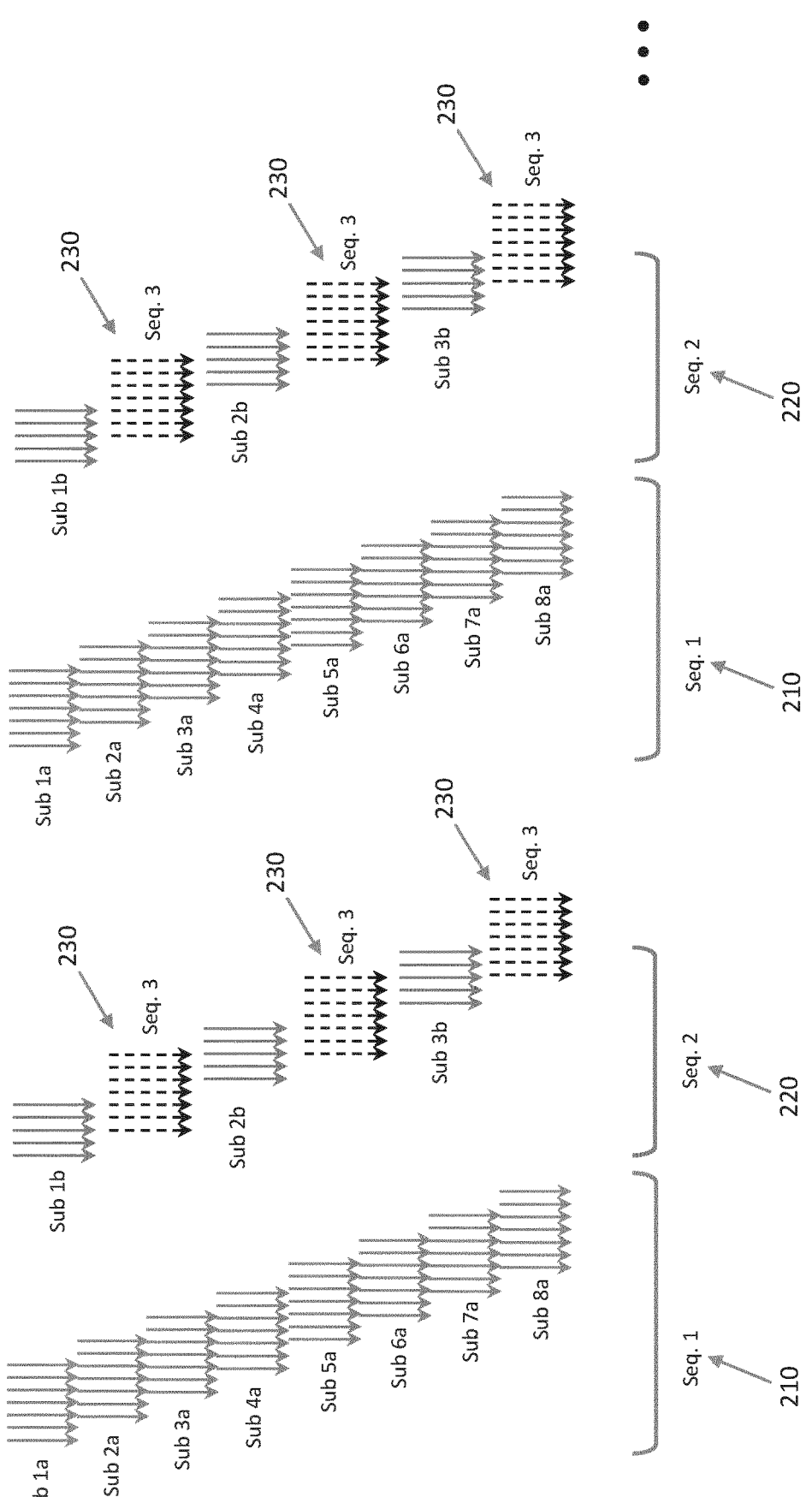
FIG. 13 shows an interleave pattern for concurrently imaging in three modes.
Figure 14:
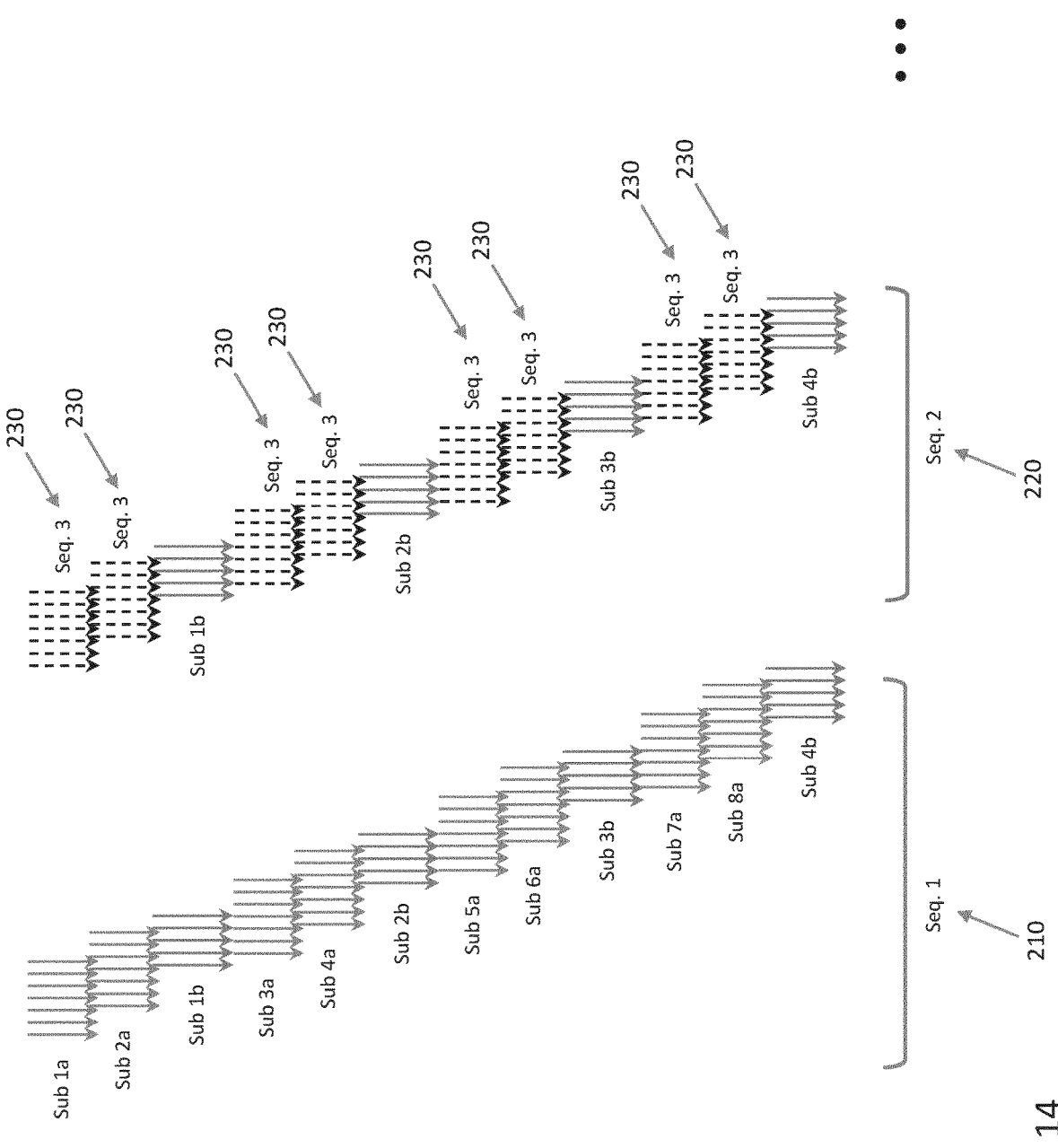
FIG. 14 shows another interleave pattern for concurrently imaging in three modes.

As mentioned herein, the system 200 may be configured to concurrently image in various combinations of 3 modes, e.g., shear-wave/Doppler/B-mode (or tissue), and contrast/Doppler/B-mode. Two examples of interleave patterns for imaging in three modes concurrently, e.g., in contrast/Doppler/B-mode, are shown in FIGS. 13 and 14. In FIG. 13, Seq. 1 acquires a 3D frame 210 (e.g., a 3D contrast frame) through a plurality of sub sequences (e.g., Sub 1a through Sub 8a) representing the collection of acquisitions at each plane of the 3D volume. Seq. 2, corresponds to the ensembles of pulses needed to acquire a Doppler image, and Sequence 3 corresponds to the B-mode frame. As shown in this example, the acquisitions are arranged so that the 3D (e.g., contrast) frame 210 finishes completely, then the Doppler and B-mode frames 220 and 230, respectively, are interleaved in any suitable pattern, which will typically be driven by the timing requirement of the Doppler ensembles (e.g., Subs 1b-3b). This sequence may correspond to the default (e.g., balanced setting) of the priority control. In the example in FIG. 14, the acquisitions for are arranged such that the Doppler acquisitions are interleaved with the 3D (e.g., contrast) frame and with the 2D (e.g. B-mode) frames, so that the Doppler frame updates also during the contrast imaging mode, rather than only during the tissue imaging. This interleave pattern may be selected when the priority of the Doppler mode is increased. Of course, the various non-limiting examples of interleave patterns for 2-mode and 3-mode combined/concurrent imaging are providing for illustration purposes and it will be understood that various other interleave patterns 231 may be defined. e.g., by the system 200 based on the rules 233 and/or pre-defined and stored in the memory 230.

In some embodiments, the rules 233 may be set to keep Doppler ensembles in a particular timing sequence that ensures accurate Doppler shift measurements, and may interleave other modes without disrupting the Doppler ensembles when priority of the modes is adjusted (e.g., by the user or system). In some embodiments, the rules 233 may define the interleave pattern based on ratios of the modes, which may be based on the selected priority or specified by the user. For example, if sequence 1 produces a 3D frame composed of X number of 2D frames or images (e.g., each of the 2D slices or planes 112 in FIGS. 1, 3, and 4), and sequence 2 consists of Y number of 2D frame (e.g., 2D slices or planes), then the number of frames of the shorter sequence (let's assume sequence 2) that can be acquired, in an interrupting or interleaved manner with the longer sequence (here, sequence 1) would be equal to the ratio X/Y. For example, if sequence 1, which produces a 3D frame composed of 8 2D frames and sequence 2 is composed of 1 2D frame, the maximum number of sequence 2 frames that can be interspersed between the 2D frames of sequence 1 is $X/Y=8/1=8$. Thus, at highest priority setting for sequence 2, the frame rate of sequence 2 may be increased by adding 7 additional frames. If the sequence 2 is composed of 2 frames, the ratio becomes $8/2=4$, thus enabling the frame rate of sequence 2 to increase by 3 additional frames, and so on. The ratios would depend on the actual number of frames that compose the longer sequence, thus making the selection of even-numbered frames a better choice for the longer sequence in terms of possibilities for defining different interleave patterns.

Figure 15:
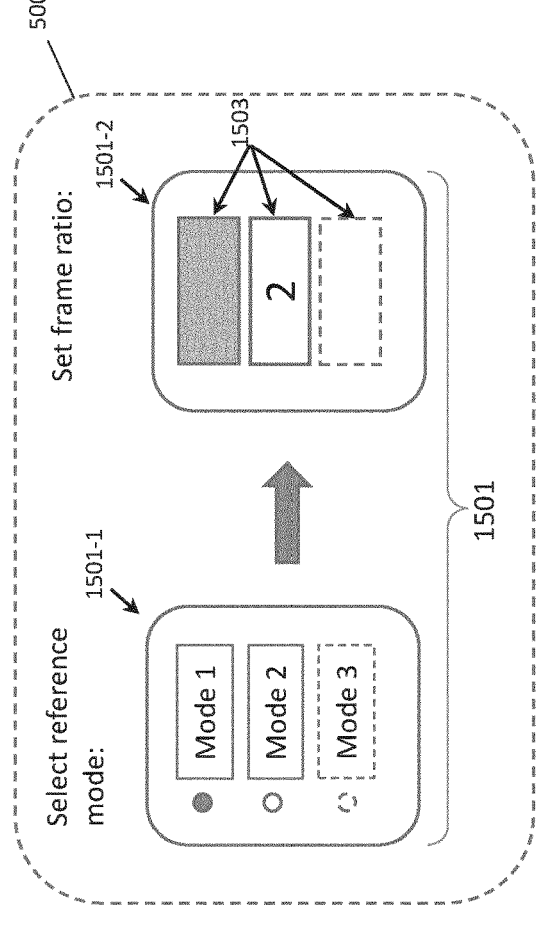
FIGS. 15 and 16 show additional examples of user controls for selectively prioritizing one of the imaging modes over other ones of the imaging modes.

With reference now to the example in FIG. 15, a user interface (UI) element 1501 may be implemented to enable the user to specify the frame ratio based on which the interleave pattern is defined by the system. The UI element 1501 has two components including a first control 1501-1 configured to enable the user to select one of the plurality of modes as a reference mode. Upon selection of a reference mode, the UI element 1501 presents a second control 1501-2 which enables the user to specify the frame ratio (e.g., the number of frames of the non-reference mode(s) to be captured for each frame of the reference mode). This control 1501-2 may be implemented by simple text input boxes 1503, or by displaying the available ratio options, which are selectable by the user. Based upon the input received via the UI element 1501, the system (e.g. processor 238) may select from the plurality of interleave patterns 231 or define an appropriate pattern based on the rules 233 that achieves the desired frame rate.

Figure 16:
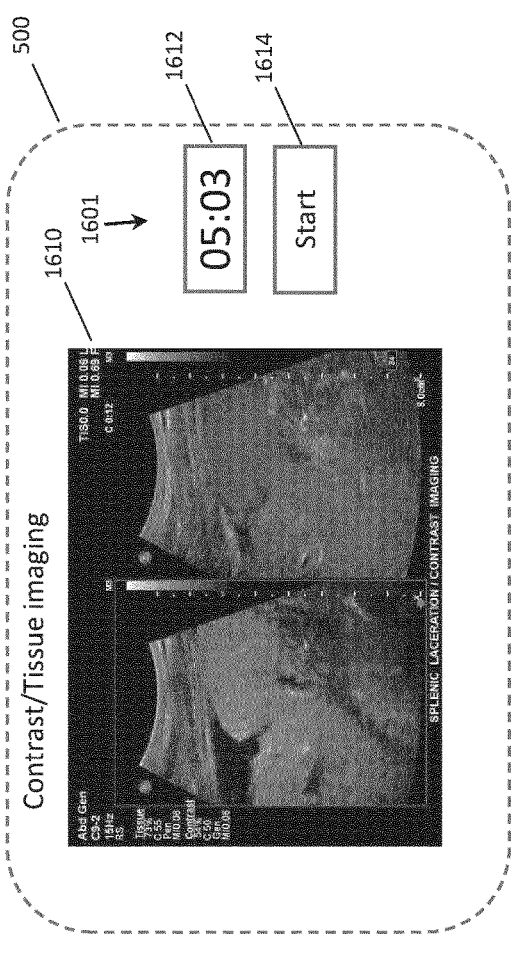

FIG. 16 shows yet another example of a UI element 1601 that effectuates an adjustment to the mode priority, e.g., a change from the default setting. The UI element 1601 may be configured to cooperate with a scanning exam protocol, whereby a certain condition that must be met is defined by the scanning protocol and the change of priority is automatically applied by the system responsive to the occurrence of the condition. As such, the change of priority may be automatically triggered by a transition into another imaging objective for which a different imaging balance may be advantageous. In some embodiments, the transition that triggers an automated priority adjustment (e.g., not requiring a user-specified priority setting, but instead the setting being automatically set by the system 200) may be additionally or alternatively tied to a timer (e.g., a CEUS timer) or other type of trigger (e.g., an EKG signal). The UI element 1601 of the example in FIG. 16 is provided in connection with a CEUS exam which acquires contrast and tissue frame, shown side by side in image display area 1610, which may be provided on the control panel 500 and/or on a main display (e.g., display 252-2) of the system. At the start of the exam, prior to injecting the contrast agent, the exam may apply a default priority, which may be neutral (balancing both modes or prioritizing the tissue mode) or which may be set by the user. The priority may be automatically adjusted at a later time (e.g., when the contrast agent is mostly stable in circulation), which may be automatically triggered by the CEUS timer, increasing the contrast mode's priority over the other mode(s). As shown in FIG. 16, the UI element 1601 includes a visible timer 1612, which is started typically at the time of the contrast agent injection, via a start button 1614. The timer 1612, which measures the time elapsed from the pressing of the start button 1614 (e.g., from the contrast injection) as the contrast passes into the patients circulation. The priority change may occur automatically after a predefined period of time after the timer has been started, which period of time may vary based upon the anatomy being imaged with CEUS.

FIG. 17 shows a flow diagram of a method in accordance with principles of the present invention. The method 1700 may be implemented by system 200 for prioritizing at least one of the plurality of imaging modes during a multi-mode imaging operation. The method 1700 starts by providing a multi-mode imaging selector, such as via a GUI element on a touch screen interface, as shown in block 1710. Responsive to a user selection of the particular desired combination of multiple modes to concurrently image in, the system (e.g., processor 238) receives the combined mode selection, as shown in block 1712. The system determines whether the selected combined mode is associated with a workflow (or imaging protocol) based priority setting routine, as shown in block 1714. If such an automated priority setting routine applies, the method continues to block 1716 in which the workflow-based priority setting routine is initiated. In some embodiments, a trigger (e.g., the occurrence of a condition which may result in the generating of a trigger signal) causes the system to automatically adjust the priority and the processor 238 may automatically receive the new priority setting. In some embodiments, the trigger is based on elapsed time, as shown in block 1718. Time may be tracked from the start of a workflow routine and/or from the activation of a timer button. As shown in block 1720, at the predefined elapsed time, the system automatically adjusts the priority setting and applies (block 1737), via the transmit controller 224, the new corresponding interleave pattern, which combines the acquisitions of the multiple modes in a manner different from the interleave pattern earlier in the workflow. The system may monitor for manual override, as shown in block 1722, which may indicate the user invoking manual control of the priority setting. This option may not be available in all combined modes.

Returning to the decision point in block 1714, if the system determines that no workflow-based priority setting routine applies to the selected combined mode, the method 1700 proceeds to block 1730, where the system (e.g., processor 238) configures the priority control(s) based on the selected combined modes. In the case of a GUI, the system may select and display the appropriate combination of GUI elements associated with the selected combined modes, as shown in blocks 1732 and 1734. In the case of mechanical controls, the system may access a look up table or use another suitable mechanism for correlating each of the "slots" or switch settings of one or a group of hard controls on the control panel designated for priority setting to the appropriate priority settings associated with the selected combined mode. Upon receipt of the priority setting (e.g., by processor 238) at block 1735, the system (e.g., processor 238) selects an appropriate interleave pattern based on the priority setting received by the processor 238 as shown in block 1736. The priority setting receive by the processor may be in response to a user operating a user control, such as by turning a dial, selecting an icon or a radio button, adjusting a position of a slider, specifying a priority of at least one mode via text input. The priority setting may be input by the user via any of the examples described herein. In some embodiments, the priority setting is generated based on a two part user input including a first part specifying a mode and a second part either selecting the desired interleave pattern associated with the specified mode, or specifying a frame ratio which is used to define the desired frame rate in relation to the specified mode. Upon selection of the appropriate interleave pattern, and as shown in block 1737, the interleave pattern is applied to the array. e.g., via the transmit controller 224, whereby the system proceeds to concurrently acquire and display images, in real-time, in accordance with the selected interleave pattern.

Figure 18:
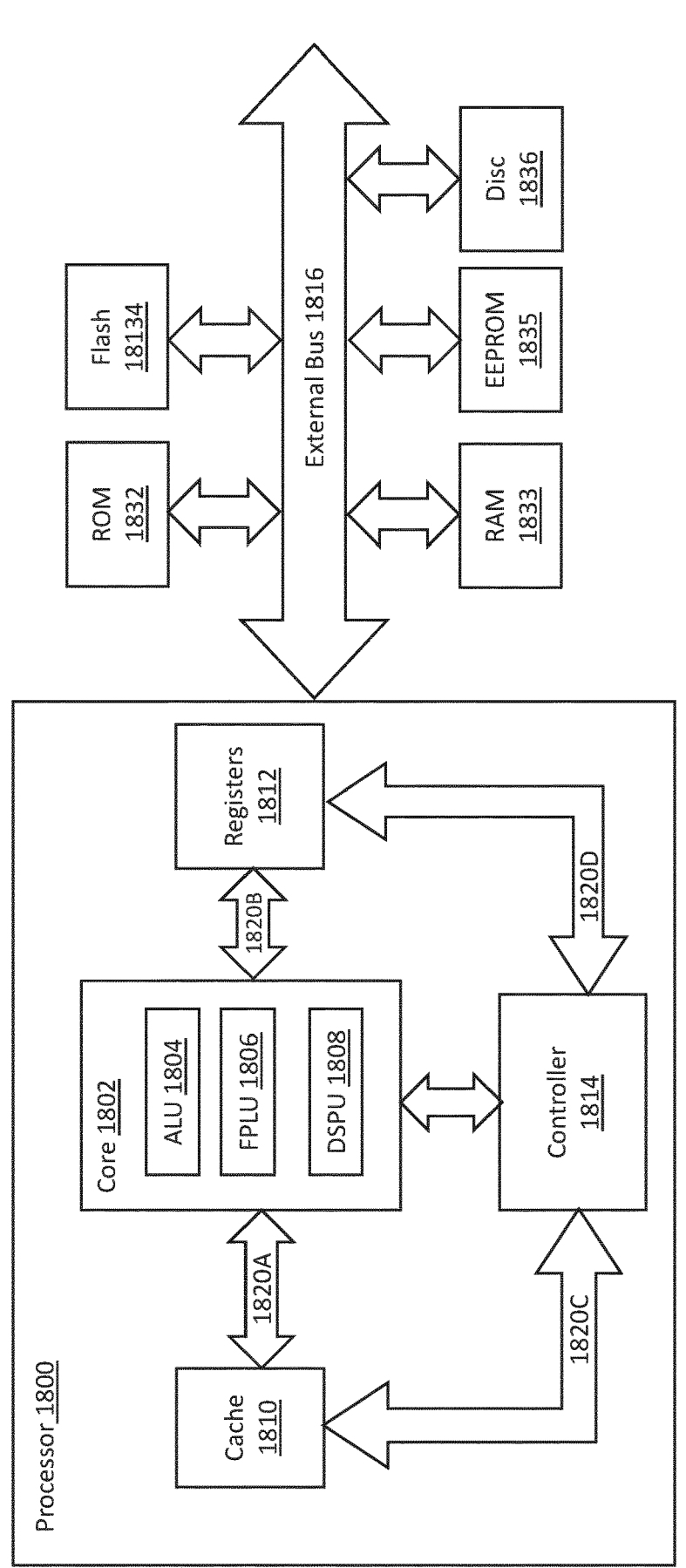
FIG. 18 is a block diagram of an example processor in accordance with the principles of the present disclosure.

FIG. 18 is a block diagram illustrating an example processor 1800 according to principles of the present disclosure. Processor 1800 may be used to implement one or more processors and/or controllers described herein, for example, the processor 240, or any of the image processor 234, system state controller 238 and/or any other processor or controller of the system 200 in FIG. 2. Processor 1800 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 1800 may include one or more cores 1802. The core 1802 may include one or more arithmetic logic units (ALU) 1804. In some embodiments, the core 1802 may include a floating point logic unit (FPLU) 1806 and/or a digital signal processing unit (DSPU) 1808 in addition to or instead of the ALU 1804. The processor 1800 may include one or more registers 1812 communicatively coupled to the core 1802. The registers 1812 may be implemented using dedicated logic gate circuits (e.g., flip-flops) and/or any memory technology. In some embodiments the registers 1812 may be implemented using static memory. The register may provide data, instructions and addresses to the core 1802. In some embodiments, processor 1800 may include one or more levels of cache memory 1810 communicatively coupled to the core 1802. The cache memory 1810 may provide computer-readable instructions to the core 1802 for execution. The cache memory 1810 may provide data for processing by the core 1802. In some embodiments, the computer-readable instructions may have been provided to the cache memory 1810 by a local memory, for example, local memory attached to the external bus 1816. The cache memory 1810 may be implemented with any suitable cache memory type, for example, metal-oxide semiconductor (MOS) memory such as static random access memory (SRAM), dynamic random access memory (DRAM), and/or any other suitable memory technology. The processor 1800 may include a controller 1814, which may control input to the processor 1800 from other processors and/or components included in a system (e.g., control panel 250 and scan converter 228 shown in FIG. 2) and/or outputs from the processor 1800 to other processors and/or components included in the system (e.g., displays 252-1, 252-2 and volume renderer 232 shown in FIG. 2). Controller 1814 may control the data paths in the ALU 1804. FPLU 1806 and/or DSPU 1808. Controller 1814 may be implemented as one or more state machines, data paths and/or dedicated control logic. The gates of controller 1814 may be implemented as standalone gates. FPGA. ASIC or any other suitable technology.

The registers 1812 and the cache memory 1810 may communicate with controller 1814 and core 1802 via internal connections 1820A. 1820B. 1820C and 1820D. Internal connections may implemented as a bus, multiplexor, crossbar switch, and/or any other suitable connection technology. Inputs and outputs for the processor 1800 may be provided via a bus 1816, which may include one or more conductive lines. The bus 1816 may be communicatively coupled to one or more components of processor 1800, for example the controller 1814, cache memory 1810, and/or register 1812. The bus 1816 may be coupled to one or more components of the system, such as display and control panel mentioned previously. The bus 1816 may be coupled to one or more external memories. The external memories may include Read Only Memory (ROM) 1832. ROM 1832 may be a masked ROM. Electronically Programmable Read Only Memory (EPROM) or any other suitable technology. The external memory may include Random Access Memory (RAM) 1833. RAM 1833 may be a static RAM, battery backed up static RAM. Dynamic RAM (DRAM) or any other suitable technology. The external memory may include Electrically Erasable Programmable Read Only Memory (EEPROM) 1835. The external memory may include Flash memory 1834. The external memory may include a magnetic storage device such as disc 1836. In some embodiments, the external memories may be included in a system, such as ultrasound imaging system 200 shown in FIG. 2, for example local memory 230.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

An ultrasound imaging system according to the present disclosure may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods. Of course, it is to be appreciated that any one of the examples, embodiments or processes described herein may be combined with one or more other examples, embodiments and/or processes or be separated and/or performed amongst separate devices or device portions in accordance with the present systems, devices and methods. Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
   a transmit controller configured to be communicatively coupled to a transducer array to cause the transducer array to transmit and receive ultrasound for imaging concurrently in a plurality of imaging modes;
   a processor configured to generate, in real-time, images from the signals received from the transducer array;
   a memory storing at least one of: a plurality of predetermined interleave patterns, and a set of predefined rules for determining an interleave pattern; and
   a user interface comprising at least one user control for prioritizing one of the plurality of imaging modes over remaining ones of the plurality of imaging modes, wherein:

the processor is further configured, responsive to receiving a priority setting during a workflow procedure and in the real-time, to select one of the plurality of predetermined interleave patterns or to determine an interleave pattern that increases a frame rate of the prioritized one of the plurality of imaging modes, and the transmit controller is configured to cause the transducer array to transmit and receive ultrasound in accordance with the interleave pattern selected or determined by the processor, wherein the at least one user control comprises one or more of a dial, a slider, a switch, one or more buttons, a graphical user interface (GUI) dial, a GUI slider, a plurality of GUI radio buttons or GUI selectable icons.

2. The system of claim 1, wherein the at least one user control is configured to selectively increase the priority of a first one of the plurality of the imaging mode with respect to the priority of a second one of the plurality of imaging modes, wherein increasing the priority of the first one of the plurality of imaging modes automatically decreases the priority of a second one of the plurality of imaging modes.

3. The system of claim 1, wherein the at least one user control is configured to enable the user to select one of the plurality of imaging modes, independent of the other imaging modes of the plurality, to be prioritized over the other imaging modes.

4. The system of claim 3, wherein the at least one user control comprises a plurality of discrete settings, only one of which is selectable at any given time.

5. The system of claim 3, wherein the plurality of discrete settings are provided by a rotary control element.

6. The system of claim 3, wherein each of the plurality of discrete settings corresponds to a different combination of a prioritized mode and associated interleave pattern type.

7. The system of claim 1, wherein the at least one user control is configured to enable the user to select a desired interleave pattern separately from setting a priority of the plurality of modes.

8. The system of claim 1, wherein the at least one user control is configured to enable the user to adjust a frame rate of at least one of the plurality of imaging modes independently of other ones of the plurality of imaging modes.

9. The system of claim 1, wherein the at least one user control comprises a control element configured to enable the user to 1) set a reference imaging mode, and 2) to specify a number of frames of a second one of the plurality of imaging modes relative to the reference imaging mode.

10. The system of claim 1, wherein the at least one user control comprises a timer which starts a timing sequence for automatically prioritizing the one of the plurality of imaging modes at a predetermined time following the activation of the timer.

11. The system of claim 1, wherein the plurality of imaging modes includes a first imaging mode, a second imaging mode, and a third imaging mode selected from the list consisting of B-mode, Doppler, contrast, and elastography.

12. A method of concurrent ultrasonic imaging in a plurality of imaging modes, the method comprising:

receiving, by a processor of an ultrasound imaging system, a combined mode selection specifying the plurality of imaging modes;

receiving a priority setting that selectively sets a priority of one of the plurality of imaging modes relative to other ones of the plurality of imaging modes;

selecting during a workflow procedure and in real-time, from among a plurality of interleave patterns associated with the plurality of imaging modes, an interleave pattern that corresponds to the priority setting;

applying the selected interleave pattern, via a transmit controller, to a transducer array to selectively activate elements of the array in accordance with a sequence defined by the selected interleave pattern for concurrently acquiring images associated with each of the plurality of imaging modes; and displaying, in the real-time, the images associated with each of the plurality of imaging modes, wherein the priority setting is generated in response to operation of a user control provided on a user interface of the ultrasound imaging system, and further wherein the operation of the user control comprises at least one of turning a dial, selecting an icon or a radio button, adjusting a position of a slider, or specifying a priority of at least one mode via text input.

13. The method of claim 12, wherein the priority setting is generated based on a two part user input including a first part specifying a mode and a second part specifying an interleave pattern associated with the specified mode or a frame ratio defined in relation to the specified mode.

14. The method of claim 12, wherein the priority setting is generated automatically at a predetermined time following activation of a timer control.

15. The method of claim 12, further comprising applying a first interleave pattern for concurrently acquiring images for each of the plurality of imaging modes, and wherein the priority setting is generated automatically in response to a trigger signal generated by the system upon the occurrence of a condition, the selected interleave pattern corresponding to a second interleave pattern that combines the acquisitions associated with each of the plurality of imaging modes in a manner different from the first interleave pattern, wherein the second interleave pattern is based on the changed relative priority of the plurality of imaging modes.

16. A non-transitory computer readable medium comprising instructions, which when executed by an ultrasound imaging system causes the system to perform the method of claim 12.

* * * * *